United States Patent [19]

Gertler et al.

[11] Patent Number: 4,828,551
[45] Date of Patent: May 9, 1989

[54] PATIENT CONTROLLED ANALGESIA APPARATUS

[76] Inventors: Robert A. Gertler, 2822 NW. 72 St., Seattle, Wash. 98117; Donald Van Nimwegen, 3329 Bella Vista South, Seattle, Wash. 98144

[21] Appl. No.: 107,780

[22] Filed: Oct. 13, 1987

[51] Int. Cl.$^4$ .............................................. A61M 5/00
[52] U.S. Cl. ................................... 604/208; 604/236
[58] Field of Search ............... 604/131, 151, 207, 208, 604/218, 246, 247, 183, 186, 191, 236; 222/381, 484–486

[56] References Cited

U.S. PATENT DOCUMENTS 4,564,360  1/1986  Young et al. ..................... 604/183
4,610,666  9/1986  Pizzino ............................ 604/191

Primary Examiner—Stephen C. Pellegrino
Attorney, Agent, or Firm—Robert W. Jenny

[57] ABSTRACT

The subject patient controlled analgesia (PCA) apparatus is mechanical/hydraulic and comprises a reservoir and a pump operable by the patient for dispensing medicine from the reservoir unto the patient's IV system in incremental doses. The pump capacity per stroke may be adjustable, thereby adjusting the size of each dose dispensed. Timing apparatus assures that a specific interval of time (the lockout interval) must pass between sequential dosage dispensations. Check valves in the passages for pumping the medicine and filling the apparatus are double in series to reduce chances of malfunction or misuse due to valve failure. The quantity of medicine in the reservoir is indicated.

12 Claims, 2 Drawing Sheets

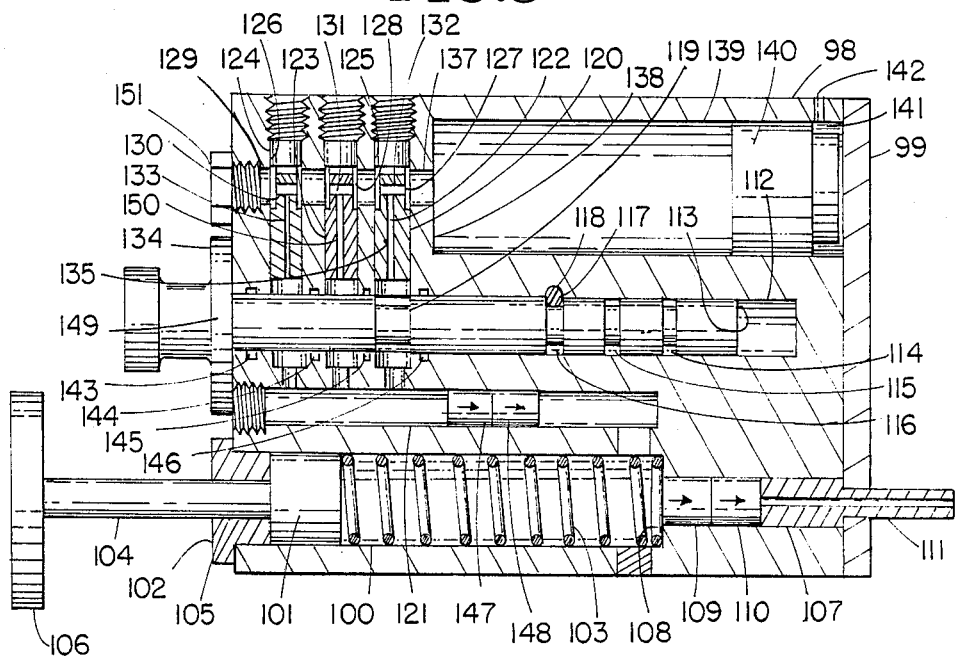
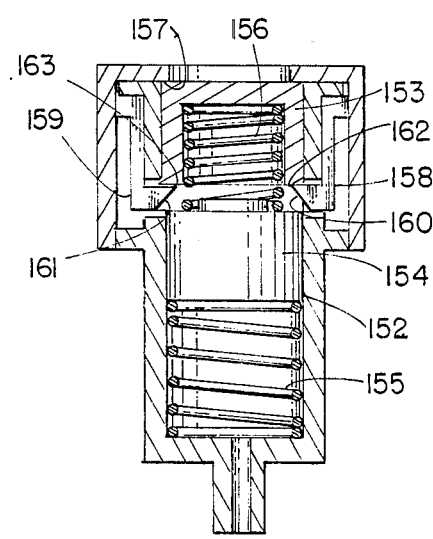
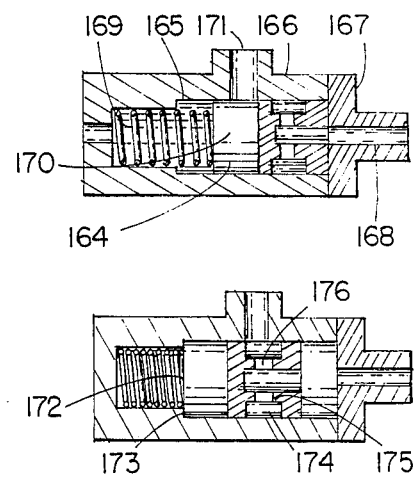

PATIENT CONTROLLED ANALGESIA APPARATUS

BACKGROUND OF THE INVENTION

1. Field:

The subject apparatus is in the field of medical apparatus, specifically apparatus involving injection of liquids into patients. More specifically, it is in the field of such apparatus which can be operated and controlled by a patient. Such apparatus is particularly applicable to the intravenous administrations of medicine intended to reduce and/or eliminate pain, i.e. pain medicine.

2. Prior Art:

It has been well established that the effectiveness of the administration of pain medicine is significantly enhanced when the medicine use can be controlled by the patient, rather than the standard procedure involving a nurse each time medicine is needed. The enhancement is manifested in terms of improvement of the patient's comfort relative to the amounts of medicine required and any adverse side effects related to the amount used and in terms of less nurse time required. With patient control, considerably less medicine is required to achieve specific levels of pain relief and the chances of and degrees of severity of side effects are correspondingly reduced.

Several kinds of patient controlled apparatus are commercially available. Generally the commercially available apparatus incorporates relatively complex electronic and electro-mechanical apparatus which enables the patient to administer an incremental dose of the pain medicine and prevents further administration for a time known as a lockout interval. The purpose of the lockout interval is to allow each dose to have its maximum effect before the next dose can be administered. The amount of medicine in each dose and the length of the lockout interval are set by the medical staff and not accessible to the patient. The commercially available apparatus is considered to be limited in its use by its cost, complication and, in some cases, questionable safety. The one non-electronic, less expensive apparatus known to be commercially available is considered to lack necessary fail-safe features.

In view of the above, a primary objective of the subject invention is provision of a patient-controlled apparatus more generally affordable than known electronic electro-mechanical PCAs. It is a further objective to provide such apparatus which is inherently safer than known apparatus regardless of cost. A still further objective is that the apparatus be easily and readily operable by both patients and medical personnel. Still further objectives may be apparent to those skilled in the art from the following descriptions of the invention.

SUMMARY OF THE INVENTION

The subject invention comprises a basic unit into which additional features may be incorporated. The basic unit comprises a reservoir filled with the medicine and a pump which is operated by the patient to pump doses of the medicine from the reservoir into the intravenous equipment in use on the patient. The supply from the reservoir to the dose pump is restricted so that only so much medicine can be pumped in a given period of time. For example, the dose pump can refill in ten minutes and therefore one full dose can be administered every ten minutes. If the pump is operated five minutes after a dose, only a half dose will result and so on. In a preferred embodiment no drug can be administered during the intervals between administrations of full doses. The dose pump has an inlet passage from the reservoir. This inlet includes the flow restriction and a double check valve to prevent flow from the pump back into the reservoir. The pump has an outlet passage in the IV system and the outlet passage has a double check valve for preventing flow back into the pump from the outlet passage. The dosage pump is a simple piston/cylinder pump with a piston rod extending from one end of the cylinder and having a push button attached to its end. The push button is accessible through a hole in the case of the unit so that the pump may be operated by insertion of a finger or the like in the hole to move the piston through the cylinder to empty the pump cylinder. A spring applies a constant force to return the piston toward and to its original position. The characteristics of the spring and the resistance element in the inlet passage, in combination with the viscosity of the medicine, determine the time for a complete refill of the pump, i.e. the duration of the lockout interval. The reservoir comprises a cylinder and piston. Ambient air pressure holds the piston against the contents of the reservoir. With the case and reservoir (or certain portions thereof) transparent, an indicator line on the piston gives visual indication of the amount of medicine in the reservoir. The cylinders and pistons of the pump and reservoir are generally similar in their details to those of conventional hypodermic devices.

A first additional feature which may be incorporated into the basic unit is a system of mechanical stops whereby the stroke of the dose pump may be limited to any one of several amounts. This feature enables administering any one of several dosage amounts from a single unit.

A second feature is a mechanism which prevents movement of the dose button in the dose administration direction once it has been first moved in that direction until it returns to or nearly to its start position. This feature assures adhering to full lockout intervals between doses.

A third feature involves visual or tactile indicators of when the dose pump is fully refilled and when the full dose has been administered, thus providing indications that a lockout interval has been completed and that the subsequent full dose has been administered.

A fourth feature provides combinations of dosage amounts and lockout interval lengths. A different restriction is used for each dosage stroke, i.e. each increment so that the interval between doses may be the same, independent of dose size selected. Mechanism adjusts the stroke and valves which direct the medicine through the appropriate passages and restrictions.

A fifth feature is that in each embodiment at least one anti-siphon device is incorporated in the medicine delivery passage. This device prevents the siphoning of medicine from the reservoir into the patient's IV system when the reservoir is positioned high enough to enable siphoning.

Various other features are incorporated to add to the safety and ease of use of the invention. The case is lockable to prevent tampering by unauthorized persons and the device may be made non-functional unless the case is closed and locked. Provisions are made for rapid filling of the apparatus and associated tubing. A check valve is used in the associated tubing to prevent the pain medicine from backing up into the main intravenous system and to prevent theft of the medicine by aspiration from the main system. The apparatus is made readily stackable with the medicine content apparent (to facilitate taking inventory) and preferably all knobs, handles, levers and the like are either within or collapsable into the envelope of the unit. In appropriate areas the case is made such that it accepts marking of patient and use related information directly on the case of the unit. Further, the unit is configured to enable secure attachment of the unit to the patient or support structure by velcro (R) tape or the like. Further, the apparatus is configured so that the main force applied to dispense a dose can be reacted by force applied by other fingers of the same hand rather than being reacted by forces in the attachment apparatus.

BRIEF DESCRIPTION OF THE DRAWINGS

FIG. 3 is a sectional, semi-schematic illustration of apparatus settable for three dose sizes and three interchangeable resistance elements for adjustment of dose size with a constant lockout interval.

FIG. 4 illustrated by sectional view apparatus which prevents dispensing a dose until the dose dispensing pump is refilled.

FIGS. 5A and 5B are a schematic illustration of an anti-siphon valve.

DETAILED DESCRIPTIONS OF THE INVENTION

Figure 1:
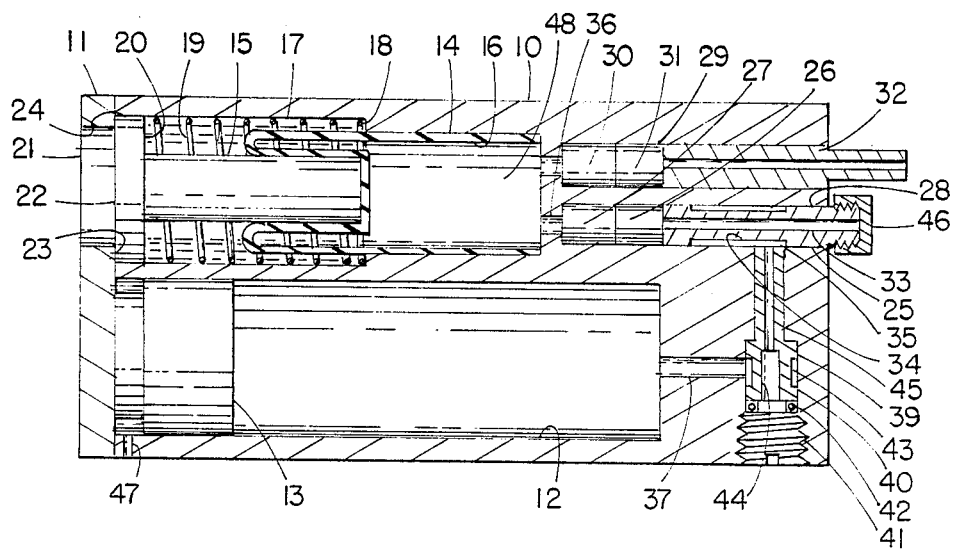
FIG. 1 is a sectional, semi-schematic illustration of apparatus for dispensing fixed sized doses with the lockout interval dependent on interchangeable flow resistance elements.

FIG. 1 is a semi-schematic, sectional illustration of apparatus for dispensing a specific amount of medicine (specific dose size) with the lockout interval duration depending on interchangeable flow resistance elements. The apparatus comprises case 10 and cap 11. Bore 12, with piston 13 slidable in the bore is a reservoir for the medicine. Bore 14 is a cylinder of the pump by which doses of medicine, i.e. quantities of liquid, are dispensed in sequence from the reservoir. Piston 15 moves axially in the cylinder with elastomeric seal 16 between the piston and cylinder. Counterbore 17 provides ledge 18 engaged by one end of spring 19. The other end engages surface 20 of head 22 of the piston. Surface 22 of the piston head contacts surface 23 of the cap. Hole 24 in the cap provides finger clearance for movement of the piston against the spring force to dispense a dose of medicine. Bore 25 in the case accepts check valves 26 and 27 and fill fitting 28. Valves 26 and 27 allow flow into the bore 14. Bore 29 accepts check valves 30 and 31 and dispense fitting 32. Valves 30 and 31 allow flow out of bore 14. Hole 33 extends from end to end of the fill fitting. Hole 34 interconnects hole 33 and groove 35 around the fitting. Medicine can flow from groove 35 to passage 36 through check valves 26 and 27 which allow flow only in the direction from groove 35 to passage 36. Passage 33 also connects with bore 39 which accepts flow restrictor fitting 40. Threaded portion 41 of fitting 40 holds the fitting in place and O ring seal 42 prevents leakage around the threaded portion. Groove 43 and hole 44 interconnect passage 37 and metering orifice 45 which connects hole 44 to groove 35. Cap 46 closes off fill fitting 28. Hole 47 vents the volume between piston 13 and cap 11.

The check valves are a type well known in the art, having a ball pressed against a seat by a spring.

For use, the unit is filled by removing the cap from the fill fitting and introducing medicine under appropriate pressure. The medicine can fill all the cavities in the unit and filling is complete when flow from the dispense fitting is steady and free of air bubbles. The fill cap is then replaced and the unit connected into the patient's IV system and attached to the patient or the IV stand, for example. A dose is dispensed by pressing the piston into the unit until it bottoms, thus expelling the medicine in cavity 48 through the dispensing fitting and the check valves in series with it. Spring force then begins to return the piston to its initial position. However, this requires flow from the reservoir through the metering orifice which has flow characteristics such that the desired lockout interval is needed for enough flow to enter cavity 48 via valves 26 and 27 to allow the piston to reach its initial position. The metering orifice establishes the duration of the lockout interval.

The entire case or an appropriate portion of it may be transparent to permit visibility of the piston and markings on it which, in combination with marking on the case, indicate how much medicine is in the unit.

The exterior of the case may be appropriately treated and/or textured in order to accept hand written marking and has appropriate shapes and protuberances to facilitate use and attachment.

The lockout interval of this unit may be varied by interchanging restrictor fittings having various sizes of metering orifices.

Figure 2:
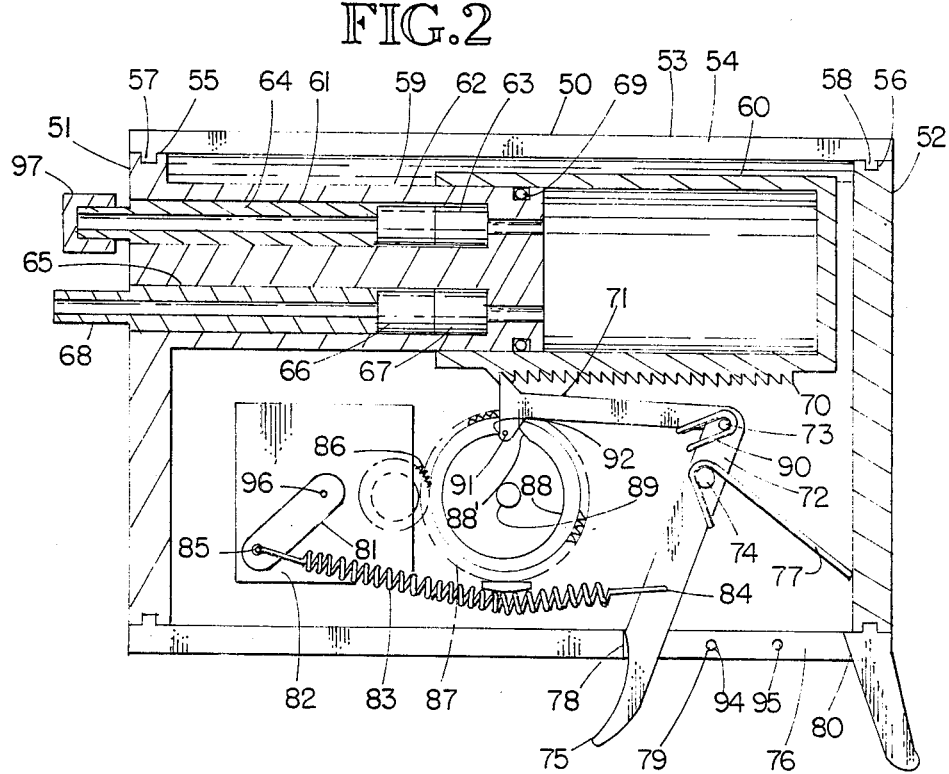
FIG. 2 is a sectional semi-schematic illustration of apparatus in which dose size is mechanically adjustable and the lockout interval is mechanically established.

The apparatus in FIG. 2, a sectional schematic view of apparatus having adjustable dosage size and lockout interval duration, the case 50 comprises ends 51 and 52 and a shell 53, made in two parts, part 54 showing and its mating part removed in this view. End 51 has groove 55 around its periphery and end 52 has groove 56 around its periphery. The shell parts have ridges 57 and 58 near their ends. The case is assembled by fitting the ridges into the grooves and attaching the shell parts together by fasteners not shown. Piston 59 extends from end 51 and cylinder 60 engages the piston telescopically. Bore 61 accomodates check valves 62 and 63 and fill fitting 64. Valves 62 and 63 allow flow only in the direction of the arrows marked on each. Bore 65 accomodates check valves 66 and 67 and dispensing fitting 68. Valves 66 and 67 allow flow only in the direction of the arrows marked on each. O ring seal 69 prevents leakage between the piston and cylinder.

Rack 70 on the cylinder is engageable by pawl 71 which is pivoted to lever 72 at center 73. Lever 72 is pivotally connected to the shell parts at 74 and end 75 of the lever extends through slot 76 between the shell parts. Spring 77 returns the lever to the position in which it is shown, stopped against end 78 of the slot. End 75 of the lever can be moved until stopped by stop pin 79 engaged in holes in the sides of the slot or until stopped by end 80 of slot 76. The lever is connected to arm 81 on timing mechanism 82 via spring 83 pivoted at 84 on the lever and 85 on the arm. Gear 86 is driven by the timing mechanism and engages gear teeth 87 on barrel cam 88 which is pivoted to a shell part at 89. Spring 90 urges pawl 71 into engagement with the teeth of rack 70. Actuating end 75 of the lever causes the pawl to advance the piston an incremental distance, thus delivering a dose of medicine. The lever movement also rotates arm 81, energizing the timing mechanism and gear 86 which in turn moves cam 88 so that surface 88' on the cam engages pin 91 on the pawl and, as the cam continues to turn, holds the pawl out of engagement with the rack until the cam has complted almost a full revolution and the pin on the pawl again clears end 92 on the cam. Engagement of pin 91 on surface 88' is effected also by the retraction motion of the pawl when the lever is released. At this point the timing mechanism automatically stops and the pawl can re-engage the rack, ready for another dispensal of medicine.

The pitch of the rack teeth is one-third the maximum distance moved by the pawl. The pawl motion can be limited to two-thirds and one-third of the maximum by installing pin 80 in one of the holes 94 and 95 respectively. According the size of the dose dispensed is limited to one- or two-thirds of the maximum by use of the pin.

The design of the timing mechanism is well within the capability of persons of ordinary skill in the art. The mechanism is similar to that of the well known cooking timer available commercially. Movement of the timer arm one-third of the maximum provides sufficient spring energy for one dispensing cycle. If the mechanism is or becomes fully wound during movement of the lever, the extra motion is accomodated by spring 83 or frictional displacement of arm 81 on shaft 96 of the timing mechanism. Timing mechanisms having a variety of cycle times may be provided, one with the desired time interval being installed in each unit as it is prepared for use.

All or a portion of the shell parts is transparent so that, with appropriate markings on the shell part(s) and cylinder, the amount of medicine in the unit is indicated.

In use, with one-half of the shell removed the desired timing mechanism is installed and the dosage size adjustment pin is put in the desired location if less than the maximum dosage is desired. The pawl is manually retracted and the cylinder moved to its position of maximum extension. The case is then assembled and preferably sealed using any of the various well known techniques used for such purposes. The unit is then filled with the medicine by removing cap 97 and introducing medicine until flow from the dispensing fitting is full and clear. Cap 97 is then replaced and the unit is ready for use, with a dose being dispensed by moving the lever. Sequential doses may be dispensed each time the timing mechanism cycles and releases the pawl for re-engagement with the rack.

FIG. 3 is a semi-schematic sectional view of a patient controlled unit having an adjustment permitting dispensing three different sized doses with a constant lockout interval duration for each dose size. However, the metering orifices for each dose size are interchangeable. The unit of FIG. 3 comprises a body 98 and a cap 99 attachable to it by means not shown. Bore 100 is a cylinder for piston 101, retained in the cylinder by cap 102 and urged toward the cap by spring 103. Piston rod 104 extends through hole 105 in the cap and push button 106 is attached to the end of the piston rod. The bore, piston rod, push button, cap and check valves 109, 110, 147 and 148 detailed later comprise a pump installed in the body. In this configuration it would be possible for the patient to pull on knob 106 to shorten the lockout interval. This could be thwarted by making piston 101 in two concentric parts, an outer cup and an inner sub-piston. In that case pulling on the knob would affect only the sub-piston and the cup can be moved only by the spring.

Bore 107 at end 108 of bore 100 accommodates check valves 109 and 110 and dispensing fitting 111 threaded into place. The valves allow flow only in the direction indicated by the arrows. Bore 112 accommodates slide valve 113 which can be set in three settings, depending on which of grooves 114, 115 or 116 is engaged by pin 117 which fits in hole 118 through the body. With the slide valve in the position shown, with the pin engaging groove 116, groove 119 is indexed to align with bore 120 which extends into passage 121 and accommodates metering orifice fitting 122 which is threaded into the body. Orifice fittings 123 and 124 are similar and groove 119 will align with their bores 125 and 126 respectively when the slide valve is set with pin 117 engaging grooves 115 and 116 respectively. The metering valve fittings have grooves 127, 128 and 129 and holes 130, 131 and 132, respectively, providing flow passages from metering orifices 133, 134, and 135 to passage 137 which extends from bottom 138 of bore 139 which is the reservoir for the medicine. Piston 140 separates the medicine in the reservoir from ambient air admitted to the volume 141 by vent hole 142. O ring seals 143, 144, 145 and 146 inhibit leakage between bores 120, 125 and 126 and from bores 120 and 126 to ambient space. Check valves 147 and 148 in passage 121 allow flow only in the direction indicated by the arrows. The diameter of flange 149 on the slide valve is such that the rim of 150 of the flange extends between button 106 on the piston rod and cap 102. Thereby, the stroke of the piston in its cylinder is limited by the positioning of the slide valve so that, accordingly, the stroke motion and therefore dose sizes produced by the stroke motions over portions of the full stroke are correlated with specific metering orifices and the associated lockout times. Cap 151, at the end of passage 137 can be removed and a fitting not shown threaded into place for filling the unit with medicine. From this point medicine can fill all the cavities in the unit and filling is complete when flow from the dispensing fitting is steady and clear, after which the filling fitting is removed and replaced by cap 151 which is sealed in place for security purposes.

FIG. 4 is a semi-schematic sectional illustration of a operation pacing mechanism which could be incorporated into the apparatuses of FIG. 1 and FIG. 3 to prevent operation of a dose dispensing button until the dose dispensing cylinder is essentially refilled. In bore 152, a cylinder for dose dispensing, there are two pistons, 153 and 154. Spring 155 is stronger than spring 156. To dispense a dose, both pistons are pushed into the cylinder by the user's fingers. When pressure is released piston 153 is returned immediately to stop shoulder 157 by spring 156 while the return of piston 154 is delayed by the flow of medicine into the cylinder from a reservoir through a metering orifice. Piston 153 is latched into the retracted position by latches 158 and 159 and cannot be moved again until piston 154 contacts and displaces the latches outwardly and out of contact with piston 153. In the illustration such contact is just beginning. The latches are cammed outwardly by contact of the piston with sloped surfaces 160 and 161. Straight portions 162 and 163 of the latch surfaces allow piston 153 to move between the latches and hold them out of engagement before piston 153 begins to move piston 154 out of engagement with the latches.

In each installation of any of the described embodiments it is necessary to install an anti-siphon apparatus in the tubing leading from the medicine dispensing fittings to the IV system. Otherwise, under certain conditions the medicine could be siphoned directly from the reservoir into the IV system. Anti-siphon devices are well known in the art and commercially available. They allow fluid to be moved by pressure on the inlet of the device but not by suction on the outlet. Such devices are used, for example, in multi-tank fuel systems to prevent the fuel in one tank from being siphoned into another. An example of an anti-siphon valve is shown in FIGS. 5A and 5B. Spool valve 164 slides in bore 165 in case 166. Cap 167 closes off the bore and includes inlet passage 168. The spool is urged against the cap by spring 169 and when it is against the cap land 170 on the spool valve closes off outlet port 171. Suction on the outlet port cannot open the valve. As shown in FIG. 5B, pressure on the inlet part moves the valve against the force of spring 169 until end 172 of the spool valve contacts shoulder 173, at which position groove 174 in the spool valve aligns with the outlet port and fluid flows through passages 175 and 176 in the valve into the groove and then the outlet port.

It is considered to be made clear by this description that the invention meets its objectives. The described embodiments of patient controlled units are all more affordable than electrical/electronic/mechanical apparatus which performs the same functions. The embodiments are inherently safe, particularly in view of their incorporating double check valves and anti-siphon devices and their inoperability until their cases are closed ready for filling. Each embodiment is easily and readily operable, requiring only button pushing or lever operation.

It will be understood by those skilled in the art that while various embodiments are described herein, other embodiments and modifications of those described are possible within the scope of the invention which is limited only by the attached claims.

What is claimed is:

1. Apparatus for dispensing a sequence of quantities of liquid with an interval of time between said dispensing of each of said quantities in sequence, said interval having a duration, said apparatus comprising:
   a body having a first bore which is a reservoir,
   a pump, installed in said body and having a stroke motion and a full stroke and comprising at least two check valves,
   means for operating said pump,
   a fill fitting,
   a dispensing fitting,
   a second bore in said body and a slide valve installed in said second bore being adjustable to a plurality of settings and slideable in said second bore and having a cylindrical surface and a groove in said surface,
   means for adjusting said valve to said settings so that at each of said settings said groove in said surface indexes with one of said plurality of grooves,
   a first passage in said body from said pump to said dispensing fitting,
   a first of said check valves of said pump in said first passage,
   a second passage in said body extending from said reservoir to
   a plurality of passages in said body from said second passage to said plurality of grooves,
   a third passage in said body from said plurality of grooves to said pump,
   a second of said check valves of said pump in said third passage,
   whereby setting said slide valve so that said groove in said cylindrical surface indexes with one of said plurality of said grooves around said bore provides a flow path from said reservoir to said pump via the one of said plurality of passages leading to said one of said plurality of grooves, said apparatus further comprising:
   means of limiting said stroke motion of said pump to any of a plurality of stroke portions in correlation with said means for adjusting said valve,
   whereby said stroke portions are correlated with flow to said pump from said reservoir through the passage of said plurality of passages to which said groove on said cylindrical surface of said valve is indexed.

2. The apparatus of claim 1 in which said means for establishing said interval comprises a plurality of metering orifice fittings installed in said plurality of passages, whereby each of said stroke portions is automatically associated with the interval established by one of said plurality of metering orifice fittings.

3. The apparatus of claim 2 in which there are two check valves in series in said third passage between said grooves and said pump and two check valves in series in said first passage.

4. The apparatus of claim 3, further comprising means for pacing the operation of said apparatus whereby said dispensing of said liquid can occur only at time intervals essentially equal to said duration.

5. The apparatus of claim 4 in which said means for pacing comprises:
   a casing having a bore, a first end having a hole and a second end having an outlet port,
   a first piston in said bore,
   a first compression spring between said second end and said first piston,
   a second piston in said bore,
   a second compression spring between said first and second pistons, said second spring being weaker than said first spring,
   means for latching said second piston in a position close to said first end, said means for latching comprising cam means operable by said first piston, whereby said second piston is unlatched and freed to move from said first and by interaction of said first piston with said cam means under force applied by said first spring,
   and whereby, further, when said first and second pistons are moved together and as close to said second end as possible by operation through said hole and said operation is ceased, said second spring returns said second piston to said position close to said first end and said means for latching latch said second piston into said position until said first compression spring causes movement of said first piston to interact with said cam means to unlatch said second piston.

6. The apparatus of claim 2, further comprising means for pacing the operation of said apparatus whereby said dispensing of said liquid can occur only at time intervals essentially equal to said duration.

7. The apparatus of claim 6 in which said means for pacing comprises:
   a casing having a bore, a first end having a hole and a second end having an outlet port,
   a first piston in said bore,
   a first compression spring between said second end and said first piston,
   a second piston in said bore, a second compression spring between said first and second pistons, said second spring being weaker than said first spring, means for latching said second piston in a position close to said first end, said means for latching comprising cam means operable by said first piston, whereby said second piston is unlatched and freed to move from said first end by interaction of said first piston with said cam means under force applied by said first spring, and whereby, further, when said first and second pistons are moved together and as close to said second end as possible by operation through said hole and said operation is ceased, said second spring returns said second piston to said position close to said first end and said means for latching latch said second piston into said position until said first compression spring causes movement of said first piston to interact with said cam means to unlatch said second piston.

8. The apparatus of claim 1 in which there is a third check valve in series with said second check valve in said third passage between said grooves and said pump and a fourth check valve in series with said first check valve in said first passage.

9. The apparatus of claim 8, further comprising means for pacing the operation of said apparatus whereby said dispensing of said liquid can occur only at time intervals essentially equal to said duration.

10. The apparatus of claim 9 in which said means for pacing comprises:

a casing having a bore, a first end having a hole and a second end having an outlet port, a first piston in said bore, a first compression spring between said second end and said first piston, a second piston in said bore, a second compression spring between said first and second pistons, said second spring being weaker than said first spring, means for latching said second piston in a position close to said first end, said means for latching comprising cam means operable by said first piston, whereby said second piston is unlatched and freed to move from said first end by interaction of said first piston with said cam means under force applied by said first spring, and whereby, further, when said first and second pistons are moved together and as close to said second end as possible by operation through said hole and said operation is ceased, said second spring returns said second piston to said position close to said first end and said means for latching latch said second piston into said position until said first compression spring causes movement of said first piston to interact with said cam means to unlatch said second piston.

11. The apparatus of claim 1, further comprising means for pacing the operation of said apparatus whereby said dispensing of liquid can occur only at time intervals essentially equal to said duration.

12. The apparatus of claim 11 in which said means for pacing comprises:

a casing having a bore, a first end having a hole and a second end having an outlet port, a first piston in said bore, a first compression spring between said second end and said first piston, a second piston in said bore, a second compression spring between said first and second pistons, said second spring being weaker than said first spring, means for latching said second piston in a position close to said first end, said means for latching comprising cam means operable by said first piston, whereby said second piston is unlatched and freed to move from said first end by interaction of said first piston with said cam means under force applied by said first spring, and whereby, further, when said first and second pistons are moved moved together and as close to said second end as possible by operation through said hole and said operation is ceased, said second spring returns said second piston to said position close to said first end and said means for latching latch said second piston into said position until said first compression spring causes movement of said first piston to interact with said cam means to unlatch said second piston.

* * * * *